US010078037B2

(12) United States Patent
Lison et al.

(10) Patent No.: US 10,078,037 B2
(45) Date of Patent: Sep. 18, 2018

(54) SIGNAL BASED SAMPLE PREPARATION

(71) Applicant: FEI Company, Hillsboro, OR (US)

(72) Inventors: Frank Lison, Gauting (DE); Jens Greiser, Kempen (DE); Matthias Langhorst, Hameln (DE)

(73) Assignee: FEI Company, Hillsboro, OR (US)

( * ) Notice: Subject to any disclaimer, the term of this patent is extended or adjusted under 35 U.S.C. 154(b) by 257 days.

(21) Appl. No.: 14/085,653

(22) Filed: Nov. 20, 2013

(65) Prior Publication Data

US 2014/0147832 A1    May 29, 2014

Related U.S. Application Data

(60) Provisional application No. 61/730,794, filed on Nov. 28, 2012.

(51) Int. Cl.
*G01N 1/30* (2006.01)
*G01N 1/31* (2006.01)
*G01N 21/64* (2006.01)
*G01N 35/00* (2006.01)

(52) U.S. Cl.
CPC .............. *G01N 1/30* (2013.01); *G01N 1/312* (2013.01); *G01N 21/6458* (2013.01); *G01N 35/0092* (2013.01); *G01N 35/00594* (2013.01)

(58) Field of Classification Search
CPC .............. G01N 1/312; G01N 15/1475; G01N 33/5091; G01N 1/30; G01N 35/0092; G01N 21/6458; G01N 35/00594; G02B 21/16; A61B 19/5212; A61B 2019/5408
See application file for complete search history.

(56) References Cited

U.S. PATENT DOCUMENTS

| 4,496,722 A  * | 1/1985 | Gallop ............. A61K 47/48061 544/69 |
| 5,912,729 A  * | 6/1999 | Jourdan ............... G01N 1/2806 356/36 |
| 2002/0160443 A1 | 10/2002 | Tsipouras et al. |
| 2007/0172100 A1 | 7/2007 | Lefebvre |

(Continued)

FOREIGN PATENT DOCUMENTS

| CN | 101004412 | 7/2007 |
| CN | 102321535 | 1/2012 |

(Continued)

OTHER PUBLICATIONS

Sangmi, Jun et al. "Direct Visualization of HIV-1 with Correlative Live-Cell Microscopy and Cryo-Electron Tomography", Structure, Current Biology Ltd., Philadelphia, PA, US, vol. 19, No. 11, Sep. 17, 2011 (Sep. 17, 2011) pp. 1573-1581.

(Continued)

*Primary Examiner* — Melanie Yu Brown
(74) *Attorney, Agent, or Firm* — Klarquist Sparkman, LLP

(57) ABSTRACT

Described is a system and method for detecting whether a biological event has occurred in a cellular sample, and then activating a fluidics system to fix the cell at the point in time with the event occurred. In one example, a sample preparation system includes a camera linked to a confocal microscope that is interrogating a cellular sample. Once a detectable event, such as a binding event, has occurred, the sample preparation system releases a fixative to fix the cell at the point in time when the event was detected.

31 Claims, 6 Drawing Sheets

(56) References Cited

U.S. PATENT DOCUMENTS

| | | | | |
|---|---|---|---|---|
| 2008/0073527 A1* | 3/2008 | Nakazawa | ......... | G01N 23/2252 |
| | | | | 250/307 |
| 2010/0096549 A1* | 4/2010 | Nishiyama | ......... | G01N 23/2251 |
| | | | | 250/307 |
| 2011/0065597 A1* | 3/2011 | Williams | ............. | G01N 33/557 |
| | | | | 506/9 |
| 2011/0168889 A1* | 7/2011 | Shachal | ................. | G01N 23/22 |
| | | | | 250/307 |
| 2011/0224574 A1 | 9/2011 | Sadler | | |
| 2012/0112094 A1* | 5/2012 | Kao | ......................... | G01J 3/44 |
| | | | | 250/458.1 |
| 2012/0135458 A1 | 5/2012 | Corwin | | |

FOREIGN PATENT DOCUMENTS

| | | |
|---|---|---|
| JP | 2002-514762 | 5/2002 |
| JP | 2011-089813 | 5/2011 |
| JP | 2012-149992 | 8/2012 |

OTHER PUBLICATIONS

Extended European Search Report dated Jun. 13, 2014 in EP 12 19 4654.
First Office Action for Chinese Application No. 201310614489.7, dated Jul. 26, 2017, 20 pages (with English translation).
Notice of Reasons for Rejection for Japanese Application No. 2013-244571, dated Sep. 19, 2017, 13 pages (with English translation).
Second Office Action from Chinese Application No. 201310614489.7, dated Apr. 10, 2018, 11 pages (with English translation).

* cited by examiner

SIGNAL BASED SAMPLE PREPARATION

CROSS-REFERENCE TO RELATED U.S. APPLICATION

This application claims priority to U.S. Provisional Application 61/730,794, filed on Nov. 28, 2012, the entirety of which is hereby incorporated by reference.

BACKGROUND OF THE INVENTION

Field of the Invention

The present embodiments relate to machines and methods of preparation of biological samples based on a signal generated by the sample. More specifically, the present embodiments relate to a device that uses image analysis for process control of the preparation of the sample.

Description of the Related Art

Correlative Light and Electron Microscopy (CLEM) is a well-known method that involves a set of procedures that correlates the information found in light microscopy of a sample with information from electron microscopy of that sample. However, many different procedures need to take place to prepare a sample that has been analyzed under light microscopy for use in electron microscopy. Light microscopy works for dynamic living cells, whereas electron microscopy relies upon fixed and processed samples. For example, biological specimens such as cells or tissue need to be properly prepared in various ways to stabilize them, reduce their thickness (ultrathin sectioning) and increase their electron optical contrast (staining) in order to be properly analyzed with electron microscopy.

In many cases CLEM is used to study biological events occurring within particular cells or tissues. For example, the kinetics of fluorescent proteins that are introduced into a cell can be determined and then the cell fixed for electron microscopy by taking the sample and performing a series of experiments to fix and process that sample. This allows the biological samples to be viewed them under an electron microscope. However, there is currently no comprehensive and consistent way to process samples observed through a light microscope so that they are automatically, reproducibly and conveniently processed for electron microscopy.

SUMMARY OF THE INVENTION

One embodiment is a device for controlling sample preparation that includes a microscope configured to provide images of a biological sample. Also included is an image analysis module configured to analyze the provided images to determine if a detectable event has occurred in the biological sample. A fluidics activation module is also configured to be activated if a detectable event has been determined, wherein the activation results in the treatment of the biological sample.

Another embodiment is a method in a system for controlling preparation of a biological sample. This method includes obtaining an image of a biological sample with a microscope and analyzing the image to determine if a detectable event has occurred, wherein if the event has occurred, activating a fluidics subsystem to prepare the biological sample for electron microscopy.

DETAILED DESCRIPTION

Figure 1:
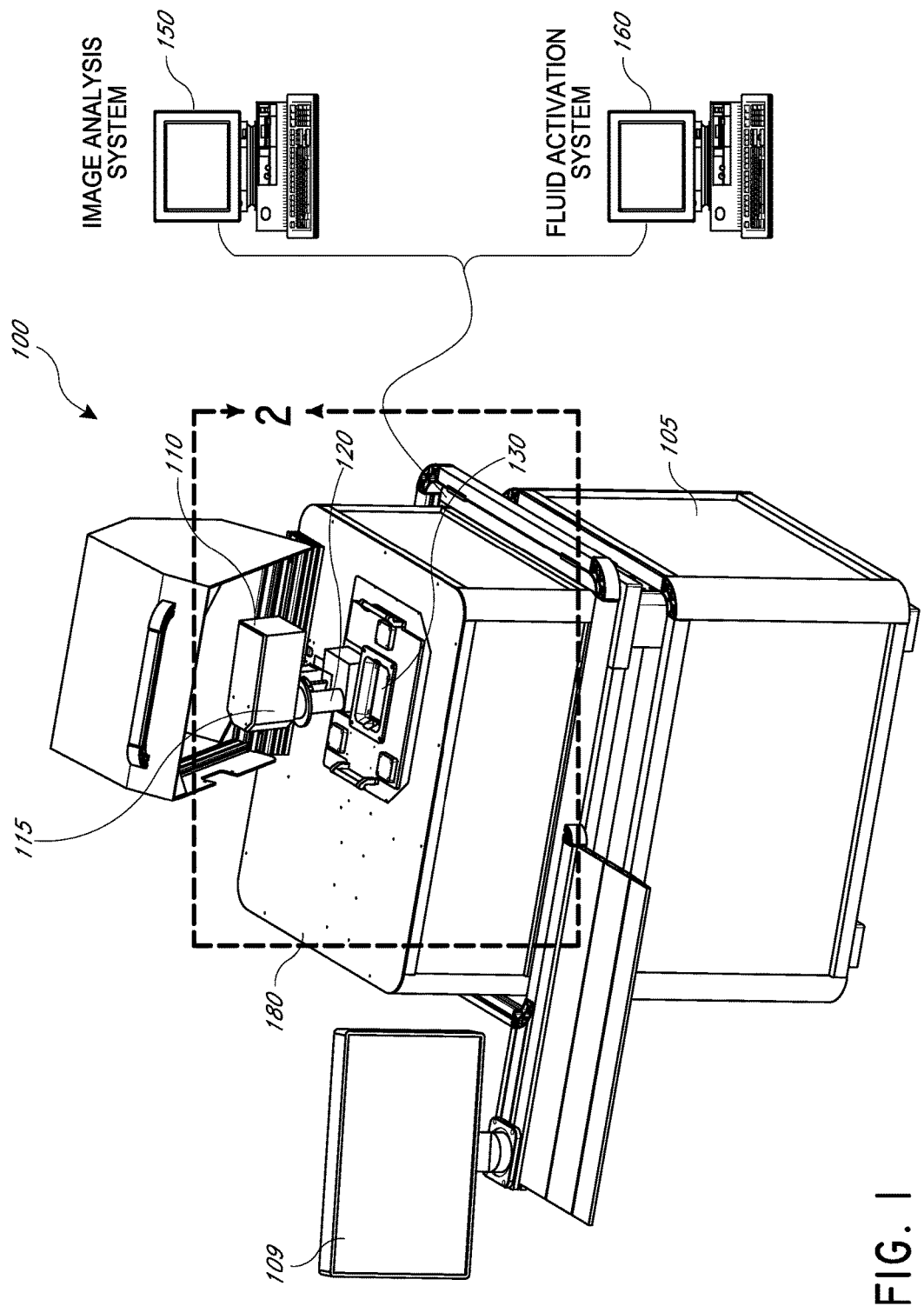
FIG. 1 is a perspective view of one embodiment of a sample preparation system.

Embodiments of the invention relate to sample processing systems and methods for preparing a biological sample for electron microscopy, or other types of further analysis. In one embodiment, the system uses a combination of light microscope imaging, captured image analysis and real-time feedback control of a fluidics system to determine if a particular cellular event has occurred, and then fix the biological sample at that point in time. For example, a sample processing system may use a high resolution camera to scan the biological sample for a detectable event, such as molecular binding, conformational change, fluorescence, or other event, and then trigger a further procedure to automatically be initialized on the biological sample. For example, the further procedure may be quick freezing the biological sample as a first step in preparing the sample for electron microscopy.

Thus, the sample processing system as described herein can provide reproducible sample preparations for electron microscopy by being tuned to, for example, always fix a particular sample whenever a predetermined biological event occurs. Thus, a series of cell samples can consistently be processed by analyzing when a fluorescent dye, or gold microsphere, attached to an antibody binds to a cell surface and then triggering a fixation reaction, as discussed below. The automated, and real-time triggering of the fixation reaction upon determination of a particular cellular event occurring under the light microscope results in a sample preparation system with very reproducible results in comparison to current systems which are triggered manually upon observation of a particular event.

One embodiment includes systems and methods that utilize an image analysis system for determining if the detectable event has occurred and a fluidics activation system for treating the sample according to the information obtained by the image analysis system. The image analysis system may be configured to receive images from any type of microscope and then analyze the image data in order to formulate a set of processing instructions to treat the sample. The fluidics activation system can be controlled by the processing instructions to activate one or more processing subsystems to release a fixation fluid onto the biological sample according to a predefined set of instructions. The sample preparation system can continue to monitor the biological sample by analyzing captured images from the microscope before, during, and/or after treatment of the biological sample.

For example, the image analysis system can analyze a series of spatial and/or temporal images captured by the microscope to determine if a particular event has occurred. Similarly, the image analysis system can analyze a series of spatial and/or temporal images during the treatment of the sample, for example to determine whether to continue or alter treatment of the sample. Additionally, the image analysis system can analyze a series of spatial and/or temporal images after treatment of the sample to determine if any errors have occurred in the preparation of the sample.

Automation of sample preparation allows for a fully automated system that can be triggered by specifically defined biological events to capture and analyze the biological sample at the moment that the specifically defined event occurred. This can advantageously increase throughput and reproducibility of sample preparations, along with providing an increased ease-of use for the sample operator. Furthermore, the sample preparation system can be integrated into a real-time control system that is used to control all phases of sample preparation for electron microscopy.

Some embodiments provide a system that is configured to process or treat a sample based on a signal generated by a biological event. Biological events of interest can be dynamic events in living samples. As discussed in more detail herein, due to real-time feedback control of sample preparation, a further advantage is that samples can be processed instantly or near instantly upon detection of the event, thereby preserving the sample in a particular state or at a particular time.

Overview of Biological Sample Treatments

Many different types of treatments can be applied to a biological sample, as discussed below. Embodiments of the invention include any type of treatment that is activated by the system described herein in response to an event being detected by the system. For example, in response to an event being detected, a chemical fixation may be initiated. In this system, the fluidics system would release a fixative that could stabilize the specimen's mobile macromolecular structure. For example, the fluidics system would release a compound with aldehydes, such as formaldehyde and glutaraldehyde to chemical crosslink proteins. Alternatively, the fluidics system may release a compound such as osmium tetroxide to fix lipid samples.

In another embodiment, the fluidics system may release compositions to cryofix the biological sample by rapidly freezing the sample. Compositions, such as liquid nitrogen, liquid ethane, or liquid helium may be used to form vitreous (non-crystalline) ice within the biological sample to preserve the ability to perform electron microscopy. This process preserves the specimen in a snapshot of its solution state at the time the detected event took place. In this embodiment, after the biological sample is cryofixed, it can then be fractured or sectioned by using a microtome and then viewed in an electron microscope.

As used herein, the term "biological sample" can include any type of sample from a biological organism, but typically includes tissue, cells, viruses, cell structures, or any other biological sample of interest Detecting Biological Events As used herein, the term "biological event" or "biological event of interest" can include, but are not limited to molecular biding (e.g., antibody binding), detection of a fluorescent molecule, receptor internalization, receptor binding, or membrane ion changes.

Biological events can be detected at one or more locations in a sample. For example, the biological event can be detected at the surface, interface, and/or in a 3-D volume. In some embodiments, the location of detection will determine the stage(s) to be used, as described in more detail herein.

Biological events can be detected through any number of techniques. For example, the event can be detected through fluorescence, reflection, interference reflection, transmitted light, and/or quantitative phase contrast in the biological sample. In some embodiments, the biological event is a label type event, such as fluorescence. In other embodiments, the biological event is a label-free type event. For example, a label-free event can include a fingerprint of a molecule in the form of a spectrum.

Biological event can take microseconds, seconds, minutes or even hours to detect. Thus, the system may monitor the sample for the detected event for time periods ranging from a few milliseconds to several hours, or more.

Embodiments of the invention include detecting biological events based on data gathered from captured images. For example, in some embodiments, the sample can be imaged in vivo and after fixation for fluorescence using common fluorescent dyes such as cyanine, fluorescein, rhodamine, Alexa Fluors, Dylight fluors, ATTO Dyes, and BODIPY Dyes. In addition, biological macromolecules such as antibodies can be labeled with a dye and used to detect the occurrence of a predetermined event.

In other embodiments, detecting the biological event does not include a label, such that the biological event can be detected from spectroscopic methods. For example, a spectrum of a sample can indicate a fingerprint of the sample. Non-label type techniques can include Coherent anti-Stokes Raman scattering (CARS) microscopy, second harmonic generation (SHG), or a combination thereof.

After an event is detected, the sample can be prepared for electron microscopy. Electron microscopy may be used in the biological and life sciences for applications such as diagnostic electron microscopy, cryobiology, protein localization, electron tomography, cellular tomography, cryo-electron microscopy, toxicology, biological production and viral load monitoring, particle analysis, pharmaceutical quality control, structural biology, 3D tissue imaging, virology, and vitrification. These separate types of applications can be performed by a range of different types of electron microscopes including, for example, transmission electron microscopes (TEM), scanning electron microscopes (SEM), reflection electron microscopes, scanning transmission electron microscopes, and low-voltage electron microscopes.

Overview of Sample Preparation System

FIG. 1 is a diagram of one embodiment of a sample preparation system 100. The sample preparation system 100 is used to prepare biological samples so that they can be transferred to an electron microscope as part of an integrated correlative microscopy system. As shown, the preparation system 100 includes a base 105 that supports an upper section 108 and a display panel 109.

Within the upper section 108 is a microscope station 110 that is used to capture images of a biological sample during processing. The microscope station 110 includes a high resolution camera 115 having a lens system 120 that can amplify and interrogate images captured from a biological sample. The camera 115 views samples that are placed within a sample holder 130, as will be described in more detail below.

Also part of the sample preparation system 100 is an analysis system 150 that is configured to analyze images of biological samples provided in the sample holder 130 and determine if a triggering event has occurred that would necessitate fixation of the sample. Also in electrical communication with the sample preparation system 100 is a fluidics activation system 160 that is configured to analyze triggering signals from the analysis system 150 and release a fixative or other type of reagent or fluid onto the sample in the sample holder 130.

It should be realized that although the image analysis system 150 and fluidics activation system 160 are illustrated as external and connected to the sample preparation system 100, then can be incorporated and part of the same system. For example, the image analysis system and fluidics activation system may be incorporated into the upper section 108 of the sample preparation system in one embodiment of the invention.

In addition, it should be realized that the present embodiments are not limited to any particular configuration of microscope. For example, any type of microscope that is used to capture images of a sample is within the scope of the present embodiments. Such microscopes include, for example, visible light microscopes, confocal microscopes, infrared and near infrared microscopes, and any other type of microscope capable of detecting events occurring within the biological sample. Those skilled in the art will recognize that embodiments exemplified herein with regard to a visible light microscope can be readily adapted to other types of microscopes.

The microscope can be configured to capture any desired series of images of the sample. In some embodiments, the microscope can be configured to continuously capture images of the sample during analysis for a predetermined event. For example, the microscope may capture images 1000, 100, 50, 10 or 1 times per second. Alternatively or additionally, the microscope may be configured to capture image(s) at selected time frames predetermined by the user of the sample preparation system.

In addition, the fluidics activation system can be connected to the sample holder through any connecting system suitable for delivering a fluid. For example, the connecting system can include any number of processor controlled microvalves, micropumps, microfluidic channels, microfluidic mixers, and/or droplet-based systems. Moreover, the connecting system of the fluidics activation system can be configured to deliver one or more fluids to the sample holder within any desired set of parameters. For example, flow rate, volume, pressure, temperature, or other parameters can be controlled by the fluidics activation system. Those skilled in the art will appreciate that the volume delivered to the sample holder can depend on the sample being treated. For example, the volume of fluid delivered can depend on the type of sample, size or thickness of the sample, or the size and configuration of the sample holder.

Any suitable fluid can be delivered to the sample holder to treat the sample. For example, in some embodiments, the delivered fluid can be a fluid for freezing a sample. Suitable freezing fluids can include liquid nitrogen, ethane, or propane. The fluid can be delivered in any desired state, for example, in a liquid, gas, or plasma state. Those skilled in the art will recognize that the selection of fluid(s) to be delivered can depend on the sample being treated and/or the desired treatment.

Moreover, the fluidics activation system may release a variety of different types of reagents as part of a sample handling procedure. For example, the fluidics activation system may cause the system to proceed to a next step in a dehydration protocol, stop a staining step or controlling the sizing of a sample as part of its protocol. In addition, the fluidics activation module can be part of an activation cycle wherein multiple biologically active compounds or molecules can be released in a predefined sequence to the biological sample. Thus, in one example, the fluidics activation module is configured to trigger release of a drug, nutrition factor, or other biologically active compound or molecule onto the biological sample as part of a treatment protocol. A final step in the treatment protocol may be the release of a fixative onto the biological sample.

Figure 2:
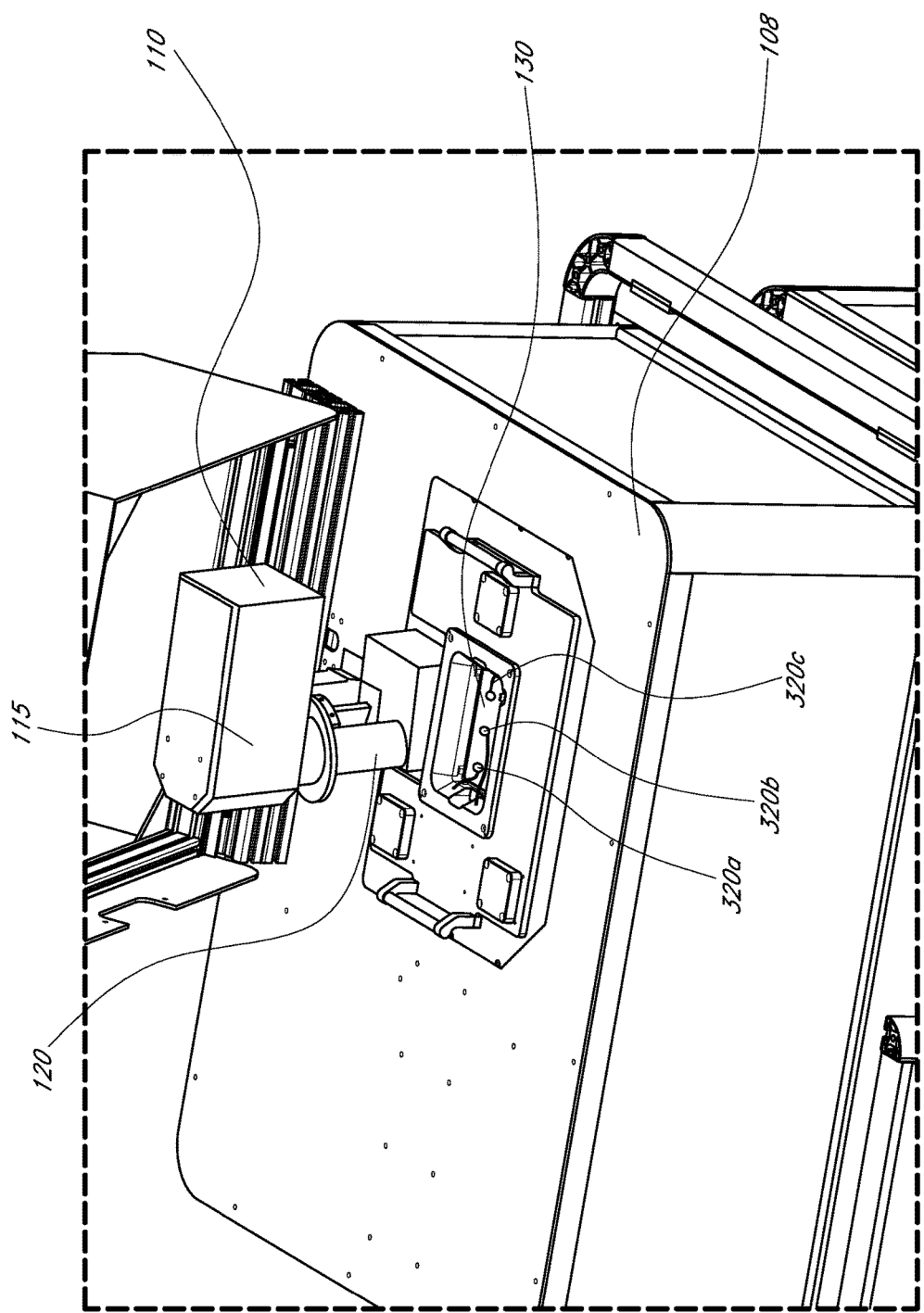
FIG. 2 is a perspective view of a microscope capturing an image of a sample holder installed within the sample preparation system of FIG. 1.

FIG. 2 is an enlarged perspective view of the upper section 108 of the sample preparation system 100 according to one embodiment. As shown, the microscope 115 is capturing an image of the sample holder 130 through the lens 120. The sample holder 130 includes a series of sample wells 320a, 320b, 320c configured to hold biological samples being analyzed in the sample preparation system 100.

Figure 3:
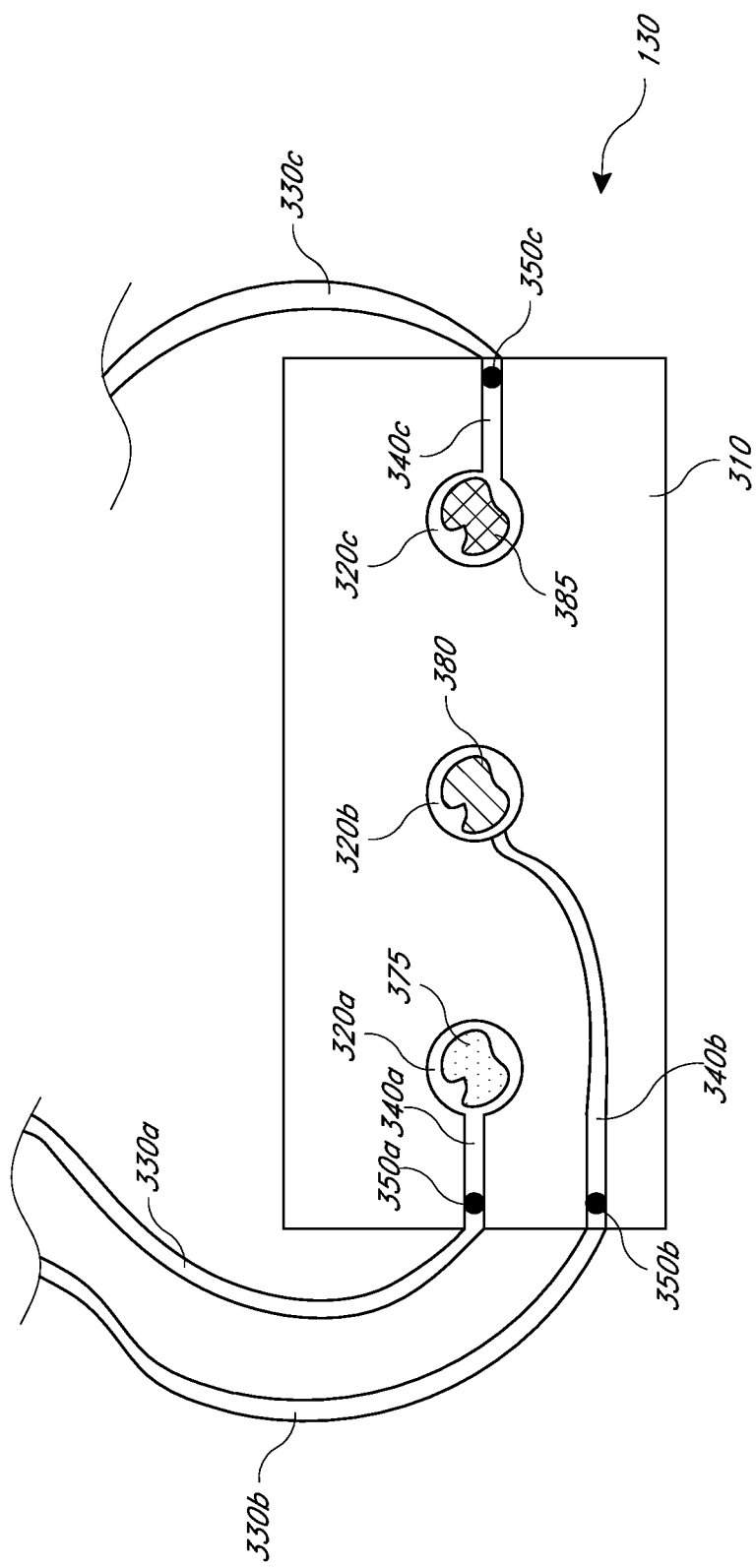
FIG. 3 is a top view of a sample holder with microfluidics channels according to one embodiment.

FIG. 3 is a top view of the sample holder 130 which includes an upper surface 310 having the sample wells 320a, 320b, 320c. The sample wells are configured to connect to fluidic tubing 330a, 330b, and 330c, to the sample preparation system 100 so that fluid can be delivered to any of the sample wells individually. For example, sample wells 320a, 320b, 320c can connect to fluid lines 330a, 330b, and 330c, respectively through fluidic channels 340a, 340b, 340c and connectors 350a, 350b, and 350c. This allows fluid introduced into any of the fluid lines 330a,b,c to be directed to a particular sample well.

As shown in FIG. 3, different types of biological samples can be placed into each of the sample wells 320a,b,c. For example, sample well 302a is shown having a set of individual cells 375 growing with in media in the well. Sample well 302b is shown as having piece of tissue 380 growing in the sample well. Finally, sample well 302c is shown as having a monolayer of cells 385 growing in the sample well.

Of course, it should be realized that the present embodiments are not limited to any particular configuration of sample holder 300 or plate holder 130. For example, any type of sample holder that used to hold a sample and allow for fluidic treatment, such as fixation, is within the scope of the present embodiments. Such sample holders include, for example, sample holders that have fewer or more sample wells. In addition, sample holders that are of different configurations, such as with two or more fluid lines connecting to each sample well are also contemplated within the scope of the present embodiments.

Figure 4:
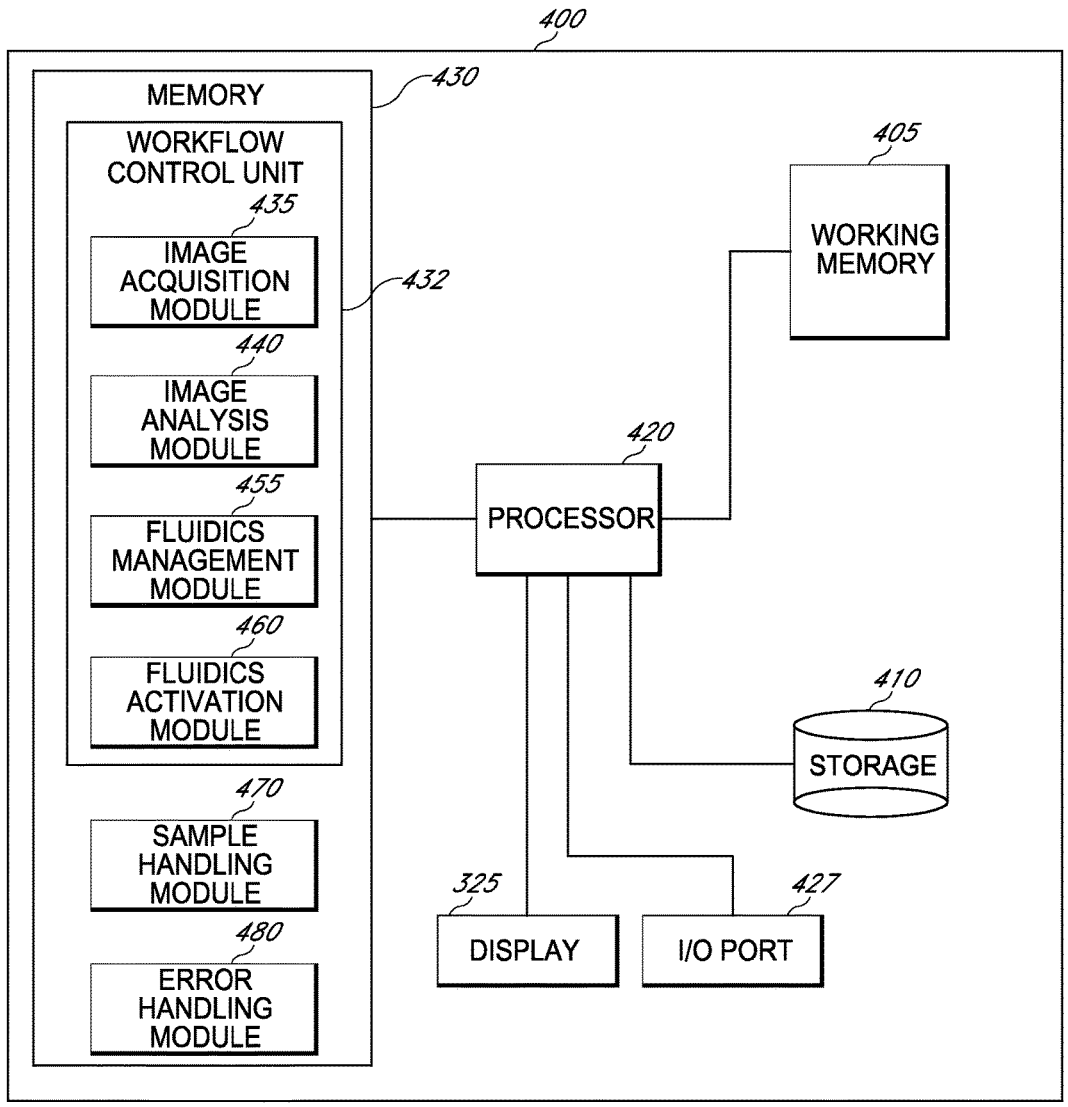
FIG. 4 is a block diagram of one embodiment of a system for preparing a sample.

FIG. 4 shows a block diagram of an exemplary implementation of a sample preparation system 400 for preparing a sample that includes an integrated image analysis system and fluidics activation system. As shown, preparation system 400 includes a processor 420 connected to a working memory 405 and non-volatile storage 410. Also connected to processor 420 are memory 430 that stores a variety of processing modules and one or more input/output (I/O) ports 427.

The memory 430 stores several modules that include software or firmware instructions used to control the actions taken by the preparation system 100. These instructions can be used to configure processor 420 to perform selected system tasks as describe more completely below.

Within memory 430 is a workflow control unit 432 that includes an image acquisition module 435, image analysis module 440, fluidics management module 455, and fluidics activation module 460. Also within the memory 430 is a sample handling module 470, and error handling module 480. The working memory 405 may be used by the processor 420 to store a working set of processor instructions contained in the modules of memory 430. Working memory 405 may also be used by processor 420 to store dynamic data created during the operation of system 100.

The workflow control unit 432 is a set of modules that act together to control the workflow of processing samples within the system 400. Within the workflow control unit 432 is the image acquisition module 435 that may include instructions that configure processor 420 to control the overall operation of the image analysis system. Image acquisition module 435 includes instructions that configure processor 420 to capture images from the camera 115 at predetermined times or according to a preprogrammed imaging protocol. The image acquisition module 435 may also include instructions that configure processor 420 to receive and/or store the captured image data from the camera to the storage 410.

The image analysis module 440 may include instructions that configure processor 420 to analyze the image data received from the image analysis system 110 to determine if a particular predetermined event has occurred. For example, the user may predetermine that the image analysis module should analyze one sample within the sample holder to determine if an internalization event has occurred within a cell. Thus, the sample would be treated with a molecule to be internalized and the system programmed to determine when the internalization event has occurred. In one embodiment, the sample is treated with a labeled molecule. The system is then programmed to capture and determine the position of cells within the sample. By determining the position and contour of cell walls within the sample, the system can, in real-time, continually plot areas of captured images that are within and external to any particular cell. The image analysis module can then determine when a particular label has crossed from being external to a cell to the interior of the cell. For example, a fluorescent dye having a particular color can be plotted over time, and when the system determines that the fluorescent dye has crossed a cell membrane boundary and entered a cell it can flag that the predetermined event has occurred.

Other embodiments may include the image analysis module being programmed to determine if a particular binding event has occurred. For example, the system may be preprogrammed to analyze for the presence of a particular labeled molecule to bind to the surface of a cell membrane. Another embodiment may be that the image analysis module is programmed to look for two labeled molecules, to be within a certain distance from one other which could indicate that the two labeled molecules had bound to one another. In other embodiments, a particular concentration of molecules in a certain region may trigger an event. For example, the image analysis module may be programmed to determine when greater than a certain number of labeled molecules have entered a cell, or bound to a cell membrane. Of course, other embodiments include a variety of ways for setting predetermined criteria for flagging that an event has occurred and aspects of the invention are not limited to any particular way of triggering that events have occurred.

It should be realized that the image analysis module 440 may include instructions that feedback to the image acquisition module 435 updates on how to capture images of a particular sample. For example, depending on analysis, the image analysis module 440 may send instruct the image acquisition module 435 to capture more, fewer, or different magnification of images in order to more clearly determine if an event has occurred.

Also within the memory 430 and connected to the image analysis module 440 is the fluidics management module 455 that includes instructions to configure processor 420 to control the overall operation of the fluidics system. For example, the fluidics management module may include instructions for determining the state of each of the fluids currently attached to the system 400. Such information may include type of fluid in each station, the temperature of each fluid, and the identification of the proper fluidics control systems, valves, and controllers to activate in order to deliver a particular fluid to the proper sample well within the sample holder. In addition, the fluidics management module 460 may include all of the protocols for properly treating a sample based on the type of fluid being use. Such protocols can include the user's pre-stored parameters for delivering a particular quantity of fluid over a particular time period, and at a particular temperature when the system has determined that an event has occurred.

In communication with the fluidics management module 455 is the fluidics activation module 460 that includes instructions to configure the processor 420 to send commands to the fluidics activation system 120 to introduce the fluids to the proper sample well. The fluidics activation module 460 can activate a sample well treatment be based on a predetermined treatment protocol generated by the fluidics management module 455. In some embodiments, activation of the sample preparation can include initialization of the fluidics activation system, for example, priming fluidics lines, adjusting fluid pressures, adjusting temperatures, or the like. However, in most cases, the fluidics activation module is configured to activate the proper valves and systems within the device 400 so that the proper fluid is delivered to the proper sample well as soon as an event is detected and flagged by the image analysis module 440.

The sample handling module 470 includes instructions that configure processor 420 to perform any particular custom routines depending on the type of sample that is resident in the sample well. For example, certain fluidics protocols may need to be performed when the sample is a tissue sample, as compared to a sample of individual cells.

The error handling module 480 includes instructions that configure processor 420 to determine if an error has occurred in the handling, processing, and/or treatment of the sample and undertaking any set error-handling processes to recover from the error Although the above described system is comprised of various modules, as can be appreciated by one of ordinary skill in the art, each of the modules may include one or more sub-routines, procedures, definitional statements or macros. Each of the modules are typically separately compiled and linked into a single executable program. Therefore, the description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

As used herein, "instructions" refer to computer-implemented steps for processing information in the system. Instructions can be implemented in software, firmware or hardware and include any type of programmed step undertaken by components of the system.

A "microprocessor" or "processor" may be any conventional general purpose single- or multi-core microprocessor such as a those manufactured by Intel, AMD, IBM or others. In addition, the microprocessor may include any conventional special purpose microprocessor such as a digital signal processor, ASIC, field programmable gate array or a graphics processor.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

The invention disclosed herein may be implemented as a method, apparatus or article of manufacture using standard programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

In addition, the modules or instructions may be stored onto one or more programmable storage devices, such as FLASH drives, CD-ROMs, hard disks, and DVDs.

Exemplary Methods for Sample Preparation

Figure 5:
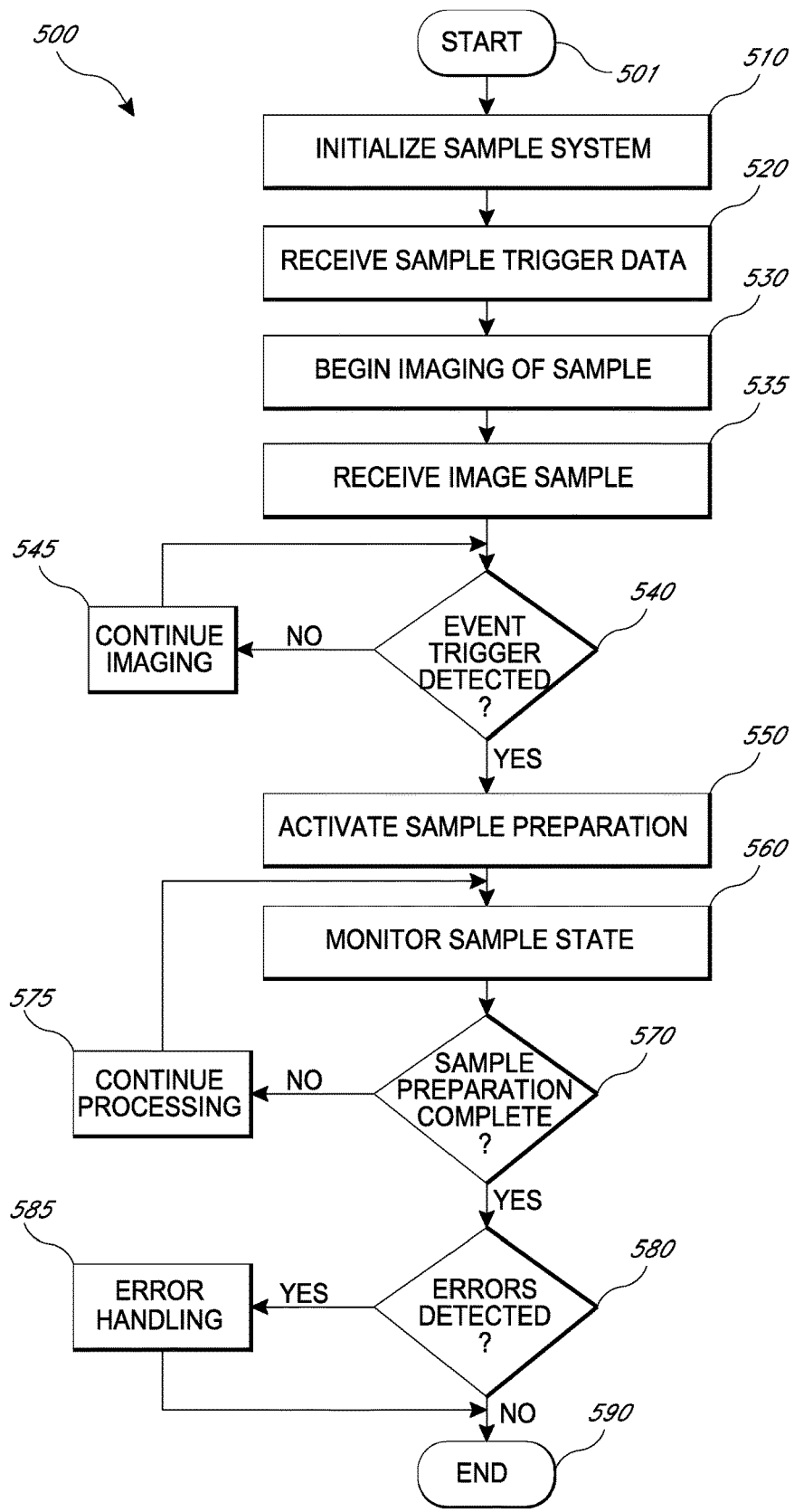
FIG. 5 is a flow diagram of one embodiment of a method for preparing a sample.

FIG. 5 shows a flowchart illustrating an exemplary process 500 that may run within one implementation of a sample preparation system 100. Process 500 may be implemented by instructions included in the memory 430, illustrated as part of device 100 in FIG. 4.

Process 500 begins at start block 501 and then moves to block 510, where the sample preparation system is initialized. For example, initialization of the sample preparation system can include initializing one or more subsystems, such as the image analysis system and/or the fluidics activation system. Once the sample preparation system is initialized, the process 500 moves to block 520, where the process waits to receive sample trigger data. The sample trigger data is the data describing the event that will trigger the release of the fluid into a sample well. Thus, as described above, the trigger data may include identification of a position of a label within a cell, or a binding event detected by the microscope, or any other event preprogrammed by the user into the system. It should also be realize that the system may simultaneously be analyzing the images captured from a plurality of sample wells to determine if any a triggering event has occurred within any sample well in the sample holder. Accordingly, a set of trigger events, one for each sample well, can be defined and stored to the system at block 520.

Once the sample trigger data has been received by the system, process 500 moves to block 530, where imaging of the biological samples within the sample block begins. For example, in some embodiments, the image acquisition module 435 can send a command to the microscope system to begin capturing images at predefined time points. Process 500 then moves to block 535, where process sample images are received by the system so that they can be analyzed by the image analysis module.

After the captured images begin to be received at the block 535, process 500 moves to decision block 540, wherein the process 500 evaluates whether a trigger event has been detected in the biological sample. This decision is normally carried out by the image analysis module 440, as discussed above. One exemplary process determining whether an event trigger has been detected is described with respect to FIG. 6 below.

Returning to FIG. 5, if an event trigger has not been detected, the method 500 moves to block 545, where the process 500 continues imaging the sample. For example, process 500 can send a new command to the microscope system to capture a new image of the samples according to a preset image capture protocol. The process 500 then returns to block 535, where process 500 receives another captured image. Returning to decision block 540, if an event trigger has been detected, then process 500 moves to block 550, where sample preparation is activated to release the predetermined fluid to the predetermined sample well.

It should be realized that while FIG. 5 shows a single loop of one event trigger being detected, and then a sample preparation being activated, embodiments also include more complicated sequences of event triggering. For example, the system may detect an event and then begin a predefined sequence of sample treatments. A first activation may be release of a drug into cell media. The system may then wait a predetermined time and release a second molecule into the media. Finally, after all treatment steps have been performed, the system may release a fixative to prepare the sample for electron microscopy. Accordingly, sample activation does not need to be a single stage process, but instead can include a variety of stages, each monitored for its own event trigger.

Once the sample preparation has been activated at block 550, process 500 then moves to block 560, where the sample state is monitored. For example, additional images can be used to monitor the sample state to determine if the sample preparation is proceeding a programmed. For example, the image analysis system can analyze the treated sample to ensure that the captured image complies with what is expected based on the type of treatment released to the sample.

Process 500 then moves to decision block 570, wherein a determination is made whether or not the sample preparation is complete. If the sample preparation is determined to not be complete then the process 500 moves to block 575 to continue processing the sample. The state of the sample can again be monitored (block 560) before returning to decision block 570. Once the sample preparation is determined to be complete at the decision block 570, process 500 moves to decision block 580 to evaluate if any errors have been detected. For example, the sample preparation may be determined to be complete only if the imaged sample is determined to be suitable for electron microscopy. If an error is detected, the process 500 moves to error handling block 585, before moving to end block 590. However, if no errors have been detected then the process 500 moves to end block 590.

Figure 6:
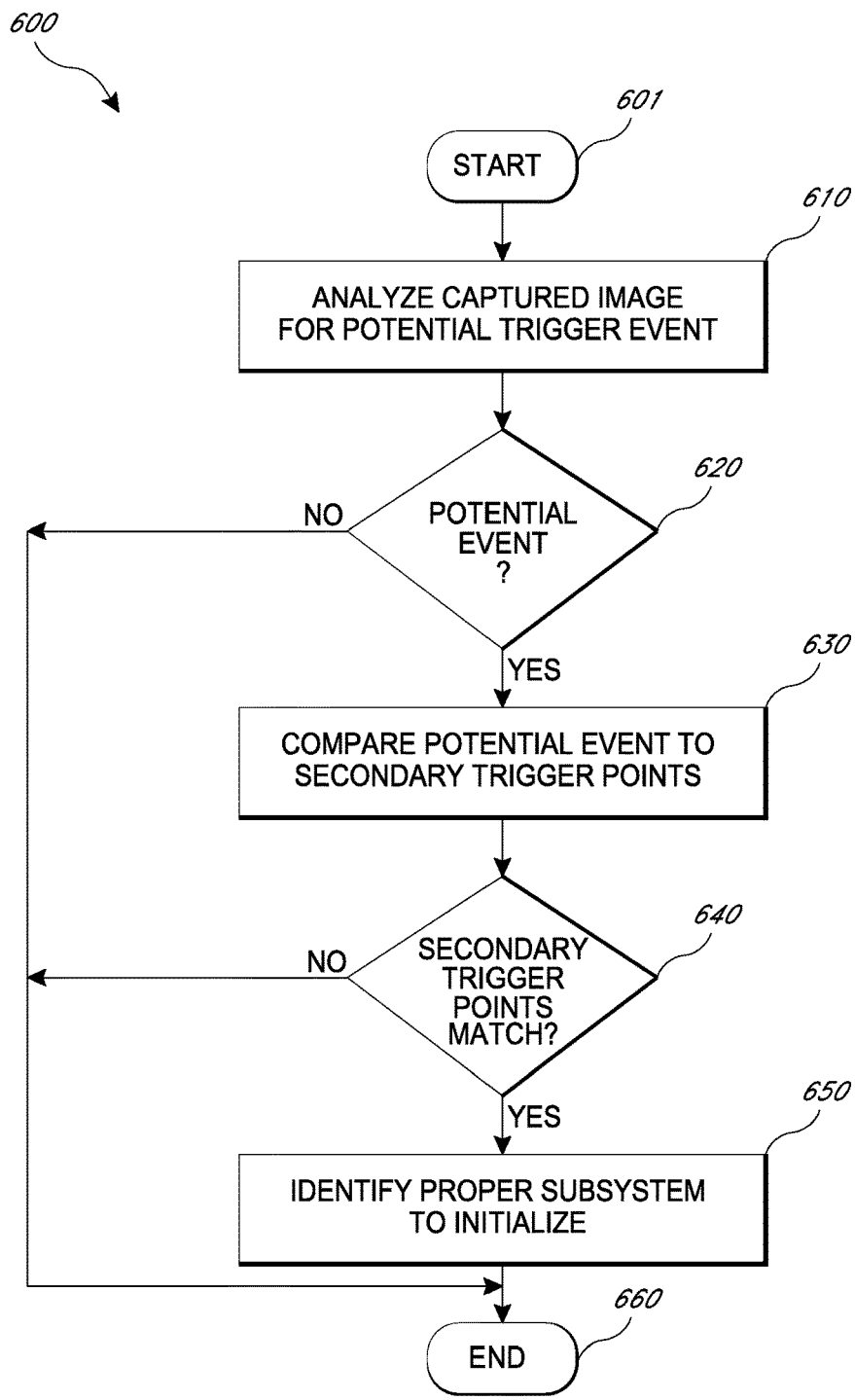
FIG. 6 is a flow diagram of one embodiment of a method for detecting an event trigger.

FIG. 6 is a flowchart illustrating an exemplary process 600 that may run within one implementation of a sample preparation system 100 for determining whether an event trigger has occurred in the biological sample. Process 600 begins at start block 601 and then moves to block 610, where a captured image is analyzed for a potential trigger event.

After analysis of the captured image, process 600 moves to decision block 620, where process 600 evaluates whether or not a potential trigger event has been detected. If a potential trigger event has not been detected, the process 600 moves to end block 660. However, if a potential trigger event has been detected, the process 600 moves to block 630, where the potential trigger event is compared to secondary trigger points.

Process 600 then moves to decision block 640, where the process 600 evaluates whether or not the potential trigger event matches the secondary trigger points. If the potential trigger event does not match the secondary trigger points, the process 600 the process moves to end block 660. If the potential trigger event matches the secondary trigger points, then process 600 moves to block 650, where one or more proper subsystems are identified for activation. Process 600 then moves to end block 650.

EXAMPLE 1

The present example outlines one embodiment of a method of preparing a sample using image-analysis for process control of the preparation steps.

An antibody labeled with a fluorescent marker is prepared. A tissue sample from a patient is contacted with the sample in order to study what changes to the cell occur upon internalization of the antibody into the cells. The sample preparation system is programed to analyze cellular images to determine the cell membrane of each cell within the sample and activated a fixation fluid when an antibody is detected as crossing a boundary of a cellular membrane.

After incubating the tissue sample and the labeled antibody, the image analysis system detects that an antibody has crossed a cellular membrane and initializes the fluidics activation system. This causes cold liquid ethane to be released into the sample well housing the tissue sample and thereby freezes the sample at the time point wherein the antibody is crossing the cellular membrane.

EXAMPLE 2

The present example outlines one embodiment of a method of preparing a sample using image-analysis for process control of the preparation steps. In this example, live mammalian cells grown on a coverslip are analyzed to determine when a particular cellular event has occurred. For example, in this example, the mammalian cells are analyzed to determine when a fluorescently labeled polynucleotide reaches a nucleus of a cell. Once this predefined trigger value is stored in system, the sample preparation system can start running in order to capture images of the mammalian cells after treatment with the labeled polynucleotides.

Although this example may use fluorescent label detection, a variety of imaging modes, such as fluorescence, reflection, interference reflection, transmitted light, (quantitative) phase contrast can be used to gather information on different sample properties. One or a combination of information on the properties is then used to determine the moment of exocytosis of a cargo vesicle into the medium based on an intensity change in a tracked vesicles. Upon detection of moment when exocytosis of the cargo vesicle is detected with the light microscope, the fluidics activation system is activated to release fixative to fix the cell in that state for electron microscopy. According to this embodiment, the sample need not be labeled at all, but rather the image analysis system is programmed to detect certain cellular events, such as exocytosis, and then activate the fluidics system.

Equivalents

The foregoing written specification is considered to be sufficient to enable one skilled in the art to practice the present embodiments. The foregoing description and Examples detail certain preferred embodiments and describes the best mode contemplated by the inventors. It will be appreciated, however, that no matter how detailed the foregoing may appear in text, the present embodiments may be practiced in many ways and the present embodiments should be construed in accordance with the appended claims and any equivalents thereof.

The term "comprising" is intended herein to be open-ended, including not only the recited elements, but further encompassing any additional elements.

What is claimed is:
1. A device, comprising:
an electronic hardware processor;
an electronic hardware memory, operably coupled to the electronic hardware processor, and storing:
an image analysis module comprising instructions stored in the electronic hardware memory, the instructions configuring the electronic hardware processor to analyze images provided by a light microscope to:
detect an individual cell in a biological sample, and
determine if a detectable biological event associated with the detected individual cell has occurred in the biological sample; and
a fluidics activation module comprising instructions that configure the electronic hardware processor to initiate treatment of the biological sample for electron microscopy in response to a determination that the detectable event has occurred based on the analyzed images associated with the light microscope.

2. The device of claim 1, further comprising the light microscope.

3. The device of claim 1, wherein the image analysis module further comprises instructions that configure the electronic hardware processor to determine a detectable event has occurred based on fluorescence in the biological sample.

4. The device of claim 1, wherein instructions in the image analysis module configure the electronic hardware processor to read at least one image every microsecond.

5. The device of claim 1, wherein the image analysis module further comprises instructions that configure the electronic hardware processor to determine if a detectable event has occurred based on detection of a fluorescent molecule.

6. The device of claim 5, wherein the biological sample is label-free and the image analysis module further comprises instructions that configure the electronic hardware processor to determine the detectable event has occurred based on a fingerprint of the molecule in the form of a spectrum.

7. The device of claim 1, wherein the image analysis module further comprises instructions that configure the electronic hardware processor to determine a detectable event has occurred based on quantitative phase contrast in the biological sample.

8. The device of claim 1, wherein the image analysis module further comprises instructions that configure the electronic hardware processor to determine if a detectable event has occurred based on detection of receptor internalization; receptor binding; or membrane ion changes.

9. The device of claim 1, wherein the image analysis module is further configured to:
detect a positon of a cell membrane for the detected cell;
detect when an antibody crosses a boundary of the detected cell membrane; and detect the biological event when the antibody crosses the boundary.

10. The device of claim 1, wherein the image analysis module is further configured to detect when a fluorescently labeled polynucleotide reaches a nucleus of the individual cell, and to detect the biological event when the nucleus is reached by the labeled polynucleotide.

11. The device of claim 1, wherein the biological sample is label-free, and the instructions stored in the electronic hardware memory configure the electronic hardware processor to analyze images provided by the light microscope to detect the individual cell in the label-free biological sample.

12. The device of claim 1, wherein the fluidics activation module comprises instructions that configure the electronic hardware processor to initiate treatment of the biological sample for electron microscopy by applying a fixative to the biological sample in response to a determination that the detectable event has occurred.

13. The device of claim 1, wherein the fluidics activation module comprises instructions that configure the electronic hardware processor to initiate treatment of the biological sample for electron microscopy by cryofixing the biological sample in response to a determination that the detectable event has occurred.

14. The device of claim 1, the instructions configure the electronic hardware processor to:
analyze a plurality of images provided by a light microscope to detect individual cells in biological samples situated in respective sample wells; and
determine if detectable biological events associated with the detected individual cells have occurred in the biological samples in each of the sample wells; and
the fluidics activation module comprising instructions that configure the electronic hardware processor to initiate treatment of the biological samples for electron microscopy in each of the sample wells for which a corresponding detectable event has been established.

15. An electronic device, comprising:
a microscope configured to provide images of a biological sample; and
an electronic hardware processor configured to perform a method of activating a fluidics subsystem, the method comprising:
detecting an individual cell in an image of the biological sample obtained with the microscope;
analyzing the image to determine if a detectable biological event associated with the individual cell has occurred; and
initiating activation of the fluidics subsystem to prepare the biological sample for electron microscopy in response to detecting the biological event associated with the individual cell has occurred.

16. The electronic device of claim 15, wherein the electronic hardware processor is configured to determine the detectable event has occurred based on fluorescence.

17. The electronic device of claim 15, wherein the electronic hardware processor is configured to determine the detectable event has occurred based on detection of a fluorescent molecule.

18. The electronic device of claim 17, wherein the electronic hardware processor is configured to determine the detectable event has occurred based on a fingerprint of the molecule in the form of a spectrum.

19. The electronic device of claim 15, wherein the electronic hardware processor is further configured to determine a detectable event has occurred based on at least quantitative phase contrast in the biological sample.

20. The electronic device of claim 15, wherein the electronic hardware processor is further configured to determine if a detectable event has occurred based on detection of receptor internalization; receptor binding; or membrane ion changes.

21. The electronic device of claim 15, wherein the electronic hardware processor is further configured to determine a detectable event has occurred based on at least interference reflection in the biological sample.

22. The electronic device of claim 15, wherein the electronic hardware processor is further configured to determine a detectable event has occurred based on at least Coherent anti-Stokes Raman scattering (CARS) microscopy in the biological sample.

23. The electronic device of claim 15, wherein the electronic hardware processor is further configured to determine a detectable event has occurred based on at least second harmonic generation (SHG) in the biological sample.

24. The electronic device of claim 15, wherein the electronic hardware processor is further configured to determine a detectable event has occurred based on at least third harmonic generation in the biological sample.

25. The electronic device of claim 15, wherein the method the processor is configured to perform further includes detecting when a fluorescently labeled polynucleotide reaches a nucleus of the individual cell, and detecting the biological event when the nucleus is reached.

26. The electronic device of claim 15, wherein the method the electronic hardware processor is configured to perform further includes detecting when a fluorescently labeled polynucleotide reaches a nucleus of the individual cell, and detecting the biological event when the nucleus is reached.

27. The device of claim 11, wherein the instructions stored in the electronic hardware memory configure the electronic hardware processor to analyze images provided by the light microscope to detect the individual cell in the label-free biological sample based on a spectrum associated with the label-free biological sample.

28. The device of claim 11, wherein the instructions stored in the electronic hardware memory configure the electronic hardware processor to analyze images provided by the light microscope to detect the individual cell in the label-free biological sample based on coherent anti-Stokes Raman scattering or second harmonic generation.

29. The electronic device of claim 15, wherein the fluidics system is configured to prepare the biological sample for electron microscopy in response to detecting the biological event has occurred by cryofixing.

30. The electronic device of claim 15, wherein the fluidics system is configured to prepare the biological sample for electron microscopy in response to detecting the biological event has occurred by applying a fixative.

31. The electronic device of claim 15, wherein the processor is configure to detect the biological sample in a label-free biological sample.

* * * * *